Figure 1:
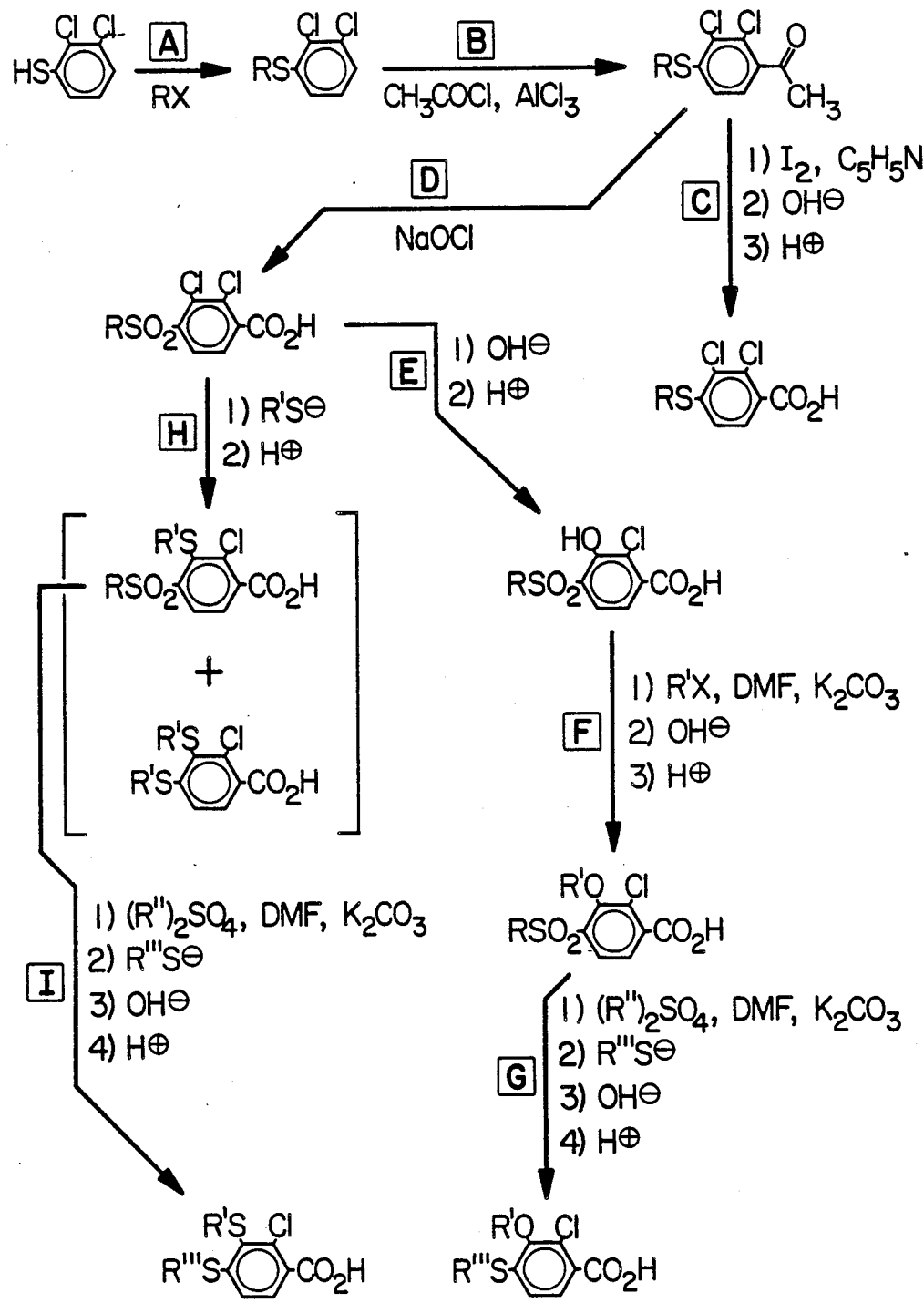

United States Patent [19]

Lee

[11] Patent Number: 4,898,973

[45] Date of Patent: Feb. 6, 1990

[54] TRISUBSTITUTED BENZOIC ACID INTERMEDIATES

[75] Inventor: David L. Lee, Martinez, Calif.

[73] Assignee: ICI Americas Inc., Wilmington, Del.

[21] Appl. No.: 709,006

[22] Filed: Mar. 7, 1985

[51] Int. Cl.$^4$ ............................................. C07C 149/40
[52] U.S. Cl. ..................................... 562/429; 562/432
[58] Field of Search ................................ 562/429, 432

[56] References Cited

U.S. PATENT DOCUMENTS 3,663,615  5/1972  Ziegler et al. .................. 562/429 X
3,878,240  4/1975  Kuenzy ........................... 562/429 X

FOREIGN PATENT DOCUMENTS 0198464  11/1983  Japan .................................... 562/432

*Primary Examiner*—Michael L. Shippen

*Attorney, Agent, or Firm*—Edwin H. Baker

[57] ABSTRACT

Novel trisubstituted benzoic acid intermediates which are useful in the preparation of certain herbicidal 2-(2,3,4-trisubstituted benzoyl)-1,3-cyclohexanediones. The intermediate benzoic acids of this invention have the following structural formula

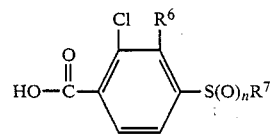

wherein $R^6$ is chlorine, $C_1$-$C_4$ alkoxy, $C_1$-$C_4$ alkylthio or hydroxy; n is the integer 0 or 2; and $R^7$ is $C_1$-$C_4$ alkyl.

8 Claims, 1 Drawing Sheet

TRISUBSTITUTED BENZOIC ACID INTERMEDIATES

BACKGROUND OF THE INVENTION

Certain 2-(2-substituted benzoyl)-1,3-cyclohexanedione herbicides are described in U.S. patent application Ser. Nos. 532,869, filed Sept. 16, 1983; 587,331, filed Mar. 7, 1984; 634,408, filed July 31, 1984; 532,882, filed Sept. 16, 1983; 566,077, filed Dec. 27, 1982; and 640,791, filed Aug. 17, 1984 and are incorporated herein by reference.

The herbicidal compounds can have the following structural formula

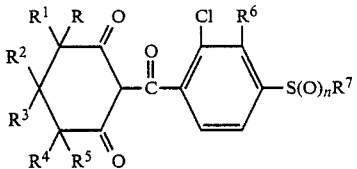

wherein R, $R^1$, $R^2$, $R^3$, $R^4$ and $R^5$ are hydrogen or $C_1$–$C_4$ alkyl; $R^6$ is chlorine, $C_1$–$C_4$ alkoxy or $C_1$–$C_4$ alkythio; and $R^7$ is $C_1$–$C_4$ alkyl; and n is the integer 0 or 2.

These herbicides can be prepared by reacting a dione of the structural formula

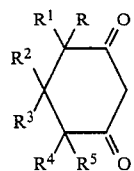

wherein R, $R^1$, $R^2$, $R^3$, $R^4$ and $R^5$ are as defined with a mole of trisubstituted benzoyl cyanides of the structural formula

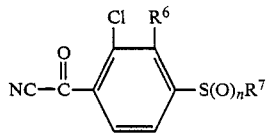

wherein $R^6$ and $R^7$ are as defined above.

A slight mole excess of zinc chloride ($ZnCl_2$) is used in a suitable solvent such as methylene chloride along with the two reactants. A slight mole excess of triethylamine is slowly added to the reaction mixture with cooling. The resulting mixture is stirred at room temperature for several hours and the reaction product is worked up by conventional techniques.

The trisubstituted benzoyl cyanides can be prepared from their corresponding tri-substituted benzoyl chlorides which are preparable from their corresponding tri-substituted benzoic acids, according to processes described in detail hereinafter.

DESCRIPTION OF THE INVENTION

This invention relates to novel trisubstituted benzoic acid intermediates which are useful in the preparation of certain herbicidal 2-(2,3,4-trisubstituted benzoyl)-1,3-cyclohexanediones, described heretofor. The intermediate benzoic acids of this invention have the following structural formula

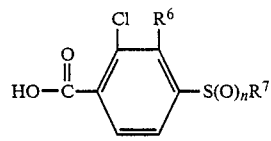

wherein $R^6$ is chlorine, $C_1$–$C_4$ alkoxy or $C_1$–$C_4$ alkylthio, n is the integer 0 or 2; and $R^7$ is $C_1$–$C_4$ alkyl, preferably $C_1$–$C_3$ alkyl.

Preferably $R^6$ is chlorine, methoxy or ethoxy or propoxy; n is 2; and $R^7$ is methyl or ethyl.

The novel intermediate having the structural formula

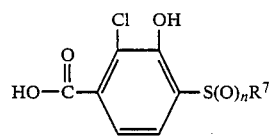

wherein n and $R^7$ are as defined are also compounds of this invention.

The intermediate compounds of the present invention can be prepared by the general method shown in FIG. 1 of the drawing with R, R', R" and R'" being $C_1$–$C_4$ alkyl groups.

Referring to FIG. 1 and particularly to Reaction Steps (A) through (I), consider the following: Generally in the reaction step (A) mole amounts of 1-mercapto-2,3dichlorobenzene and an alkylating agent (RX) such as $C_1$–$C_4$ alkyl halide, e.g.,=ethyl chloride are reacted along with a slight mole excess of an acid acceptor such as potassium carbonate. The two reactants and the potassium carbonate are combined in a suitable solvent such as acetonitrile. The reaction mixture is heated to about 80° C. for 1–3 hours. The reaction product is recovered by conventional techniques.

For reaction (B), the 1-($C_1$-$C_4$-alkylthio)-2,3-dichlorobenzene (1 mole) and acetyl chloride (2 moles) are reacted along with 2 moles of aluminum chloride or zinc chloride added slowly in a suitable solvent such as ethylene chloride or methylene chloride at a temperature of about 0° to 5° C. for 1–2 hours. After the reaction mixture is allowed to warm to room temperature, it is added to a mixture of ice and 2 normal hydrochloric acid. Aqueous and solvent layers form and are separated. The desired 4-($C_1$-$C_4$-alkylthio)-2,3-dichloroacetophenone is recovered from the solvent by conventional techniques.

The novel intermediate compounds, 4-($C_1$-$C_4$-alkylthio)-2,3dichlorobenzoic acid, can be prepared in reaction step (C) by oxidizing a mole amount of the 4-($C_1$-$C_4$-alkylthio)-2,3-dichloroacetophenone prepared in reaction step (B) with at least a mole amount of iodine in pyridine followed by hydrolysis with sodium hydroxide in a manner as described by L. C. King, *J. Amer. Chem. Soc.*, 66, 894 (1944). The desired intermediate compounds are recovered by conventional techniques.

In the alternative, another novel intermediate compound 4-($C_1$-$C_4$-alkylsulfonyl)-2,3-dichlorobenzoic acid can be prepared in reaction step (D) by oxidizing a mole amount of 4-($C_1$-$C_4$-alkylthio)-2,3-dichloroacetophenone prepared in reaction step (B) with at least 5 moles of an oxidizing agent such as sodium hypochlorite in a suitable solvent such as dioxane by heating a solution of the reactants to 80° C. After an exothermic reaction, the mixture is cooled and acidified with hydrochloric acid. The desired intermediate which is a precipitate is recovered by filtration.

In reaction step (E) 4-($C_1$-$C_4$-alkylsulfonyl)-2,3-dichlorobenzoic acid prepared in reaction step (D) is dissolved in a 20% aqueous solution of sodium hydroxide and heated at reflux for 5-10 hours. The resulting mixture is cooled and acidified with an acid such as concentrated hydrochloric acid. The crude acid is recovered by extracting it with ethyl acetate, followed by drying over magnesium sulfate and removing the ethyl acetate under vacuum. The desired novel intermediate product, 4-($C_1$-$C_4$-alkylsulfonyl)-2chloro-3-hydroxybenzoic acid, is obtained by recrystallization from ethyl acetate.

In reaction step (F), 1 mole of 4-($C_1$-$C_4$-alkylsulfonyl)-2-chloro-3-hydroxybenzoic acid prepared in reaction step (E) and an alkylating agent (R'X) (2 moles) such as $C_1$-$C_4$ alkyl iodide, e.g., ethyl iodide, are reacted along with a slight mole excess of an acid acceptor such as potassium carbonate. The two reactants and the acid acceptor are combined in a suitable solvent such as dimethylformamide and heated at 50°-100° C. for 7-24 hours. After cooling, the reaction mixture is partitioned between ethyl acette and 5% potassium carbonate. The ethyl ester of 4-($C_1$-$C_4$-alkylsulfonyl)-3-($C_1$-$C_4$-alkoxy)-2-chlorobenzoic acid is recovered from the ethyl acetate layer by conventional techniques. Basci hydrolysis of the ester yields the desired intermediate acid.

In reaction step (G), mole amounts of 3-($C_1$-$C_4$-alkoxy)-4-($C_1$-$C_4$-alkylsulfonyl)-2-chlorobenzoic acid prepared in reaction (F) and di-$C_1$-$C_2$-alkyl sulfate (R'')$_2$SO$_4$ along with 3 moles of potassium carbonate are stirred at room temperature for 0.5-1.5 hours in a suitable solvent such as dimethylformamide to form the alkyl ester of the starting trisubstituted benzoic acid. Next, 2 moles of $C_1$-$C_4$ alkylmercaptan (R'''SH) is added to the reaction mixture and stirred for several days at room temperature, whereby the 4-($C_1$-$C_4$-alkylsulfonyl) group of the ester is replaced with a $C_1$-$C_4$-alkylmercaptan group. The reaction mixture is partitioned between methylene chloride and water. The methylene chloride is concentrated in vacuo to yield the crude ester of the desired benzoic acid. After basic hydrolysis of the ester, the desired 3-($C_1$-$C_4$-alkoxy)-4-($C_1$-$C_4$-alkylthio)-2-chlorobenzoic acid is obtained.

In reaction step (H) a mole amount of 4-($C_1$-$C_4$-alkylsulfonyl)2,3-dichlorobenzoic acid (obtained in reaction step (D)), 5 moles of sodium hydroxide and 4 moles of $C_1$-$C_4$ alkyl mercaptan (R'SH) in water are heated at reflux for 24 hours. After cooling, the reaction mixture is acidified with concentrated hydrochloric acid and extracted with methylene chloride. Two layers form and are separated. The methylene chloride layer is dried over magnesium sulfate. The methylene chloride is stripped under vacuum to give a mixture of novel intermediate 4-($C_1$-$C_4$-alkylsulfonyl)-3-($C_1$-$C_4$-alkylthio)-2-chlorobenzoic acid and novel intermediate 3,4-bis(-$C_1$-$C_4$-alkylthio)-2-chlorobenzoic acid. The two benzoic acids are esterified to the methyl ester with methanol and sulfuric acid in an ethylene dichloride solvent by the procedure recited in Clinton and Laskowski, *J. Amer. Chem. Soc.*, 70, 3135 (1948). The esters are then separated by standard chromatographic techniques. Basic hydrolysis of the separated esters give the desired acids. The first acid, 4-($C_1$-$C_4$-alkylsulfonyl)-3-($C_1$-$C_4$-alkylthio)-2-chloro-benzoic acid, is obtained in higher amounts.

In reaction step (I), mole amounts of 3-($C_1$-$C_4$-alkylthio)-4-($C_1$-$C_4$-alkylsulfonyl)-2-chlorobenzoic acid prepared in reaction (H) and dialkyl sulfate (R'')$_2$SO$_4$ along with 3 moles of potassium carbonate are stirred at room temperature for 0.5-1.5 hours in a suitable solvent such as dimethylformamide to form the ethyl ester of the starting trisubstituted benzoic acid. Next, 2 moles of $C_1$-$C_4$ alkylmercaptan (R'''SH) is added to the reaction mixture and stirred for several days at room temperature, whereby the 4-($C_1$-$C_4$-alkylsulfonyl) group of the ester is replaced with a $C_1$-$C_4$-alkylmercaptan group. The reaction mixture is partitioned between methylene chloride and water. The methylene chloride is concentrated in vacuo to yield the crude ester of the desired benzoic acid. After basic hydrolysis of the ester, the desired 3-($C_1$-$C_4$-alkylthio)-4-($C_1$-$C_4$-alkylthio)-2-chlorobenzoic acid is obtained.

The following series of examples teach the synthesis of representative compounds of this invention. The structures of all compounds of the examples and tables were verified by nuclear magnetic resonance (nmr), infrared spectroscopy (ir) and mass spectroscopy (ms).

EXAMPLE 1

2,3-Dichloro-4-ethylthio-acetophenone

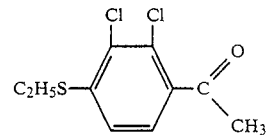

To a solution of the 2-ethylthio-2,3-dichlorobenzene (0.5 moles) and 78.5 grams (g) (1.0 mole) acetyl chloride in 500 milliliters (ml) of methylene chloride at 5° C. was added aluminum chloride (133.5 g, 1.0 mole) portionwise, over a period of 1.0 hour. The reaction was allowed to warm to room temperature, and then it was slowly poured into a mixture of ice and 2N hydrochloric acid. The layers were separated and the methylene chloride layer was washed with 5% NaOH and water. After drying over magnesium sulfate, the methylene chloride was removed in vacuo to afford the acetophenone (114 g, 90%) as a tan solid with m.p. 53°-55° C.

Additional compounds were prepared by the same procedure as described in Example 1 and are listed in Table 1.

TABLE 1

4-Alkylthio-2,3-dichloroacetophenones

| R' | Physical Constant (m.p. °C.) |
|---|---|
| —CH$_3$ | 65-72 |
| —CH$_2$CH$_2$CH$_3$ | glass |

EXAMPLE 2

2,3-Dichloro-4-ethylthiobenzoic Acid

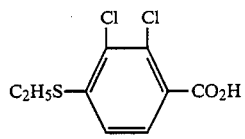

The 4-ethylthio-2,3-dichloroacetophenone prepared in Example 1 was oxidized to the corresponding acid employing iodine-pyridine and sodium hydroxide in a manner as described by L. C. King, *J. Amer. Chem. Soc.*, 66, 894 (1944). m.p. 204°–206° C.

Additional compounds were prepared by the same procedure as described in Example 2 and are listed in Table 2.

TABLE 2

4-Alkylthio-2,3-dichlorobenzoic Acids

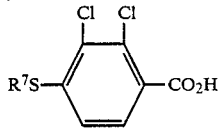

| $R^7$ | Physical Constant (m.p. °C.) |
|---|---|
| —$CH_3$ | 201–205° C. |
| —$CH_2CH_2CH_3$ | 188–190° C. |

EXAMPLE 3

4-Ethylsulfonyl-2,3-dichlorobenzoic Acid

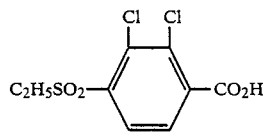

A vigourously stirred mixture of the 4-ethylthio-2,3-dichloroacetophenone prepared in Example 1 (0.25 mole), dioxane (200 ml), and 5% sodium hypochlorite (1860 ml, 1.25 mole) was slowly heated to 80° C., whereupon an exothermic reaction commenced. After the exotherm (80°–100° C.) had subsided the reaction mixture was cooled and acidified with concentrated hydrochloric acid. Filtration of the resulting precipitate then afforded the desired acid. m.p. 170°–172° C.

Additional compounds were prepared by the same procedure as described in Example 3 and are listed in Table 3.

TABLE 3

4-Alkylsulfonyl-2,3-dichlorobenzoic Acids

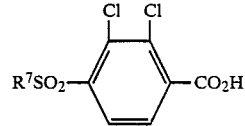

| $R^7$ | Physical Constant (m.p. °C.) |
|---|---|
| —$CH_3$ | 189–193 |
| —$CH_2CH_2CH_3$ | 202–204 |

EXAMPLE 4

2-Chloro-4-ethylsulfonyl-3-hydroxybenzoic Acid

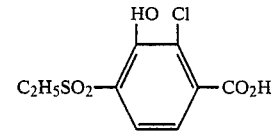

A solution of the 4-ethylsulfonyl-2,3-dichlorobenzoic acid prepared in Example 3 (0.35 mole) in 500 ml of 20% sodium hydroxide was heated at reflux for 7 hours. After cooling, the aqueous solution was acidified with concentrated hydrochloric acid and extracted twice with ethyl acetate. The ethyl acetate extracts were combined, dried over magnesium sulfate, and concentrated in vacuo to afford the crude acid. Recrystallization of the crude acid from ethyl acetate afforded the desired pure acid as white crystals. m.p. 188°–192° C.

Additional compounds were prepared by the same procedure as described in Example 4 and are listed in Table 4.

TABLE 4

4-Alkylsulfonyl-2-chloro-3-hydroxybenzoic Acid

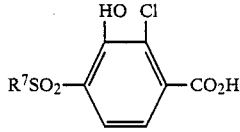

| $R^7$ | Physical Constant (m.p. °C.) |
|---|---|
| —$CH_3$ | 187–189 |
| —$CH_2CH_2CH_3$ | 181–185 |

EXAMPLE 5

3-Ethoxy-4-ethylsulfonyl-2-chlorobenzoic Acid

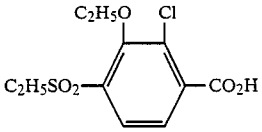

A mixture of the 2-chloro-4-ethylsulfonyl-3-hydroxybenzoic acid prepared in Example 4 (0.075 mole), ethyl iodide (0.5 mole), and potassium carbonate (0.1 mole) in dimethylformamide (150 ml) was heated at 90° C. for 7 hours. After cooling, the reaction mixture was partitioned between ethyl acetate and 5% potassium carbonate. The ethyl acetate layer was then washed with brine, dried over magnesium sulfate, and concentrated in vacuo to afford the crude ethyl ester of the desired benzoic acid. Hydrolysis of the ester to the acid was accomplished by stirring the ester (0.075 mole) with a base such as sodium hydroxide (0.1 mole) in ethanol (100 ml) at room temperature for 16 hours. The reaction mixture was acidified with 2N HCl, and then partitioned between methylene chloride and water. The methylene chloride layer was dried over magnesium sulfate and concentrated in vacuo to afford the acid as an oil.

Additional compounds were prepared by the same procedure as described in Example 5 and are listed in Table 5.

TABLE 5
4-Alkylsulfonyl-3-alkoxy-2-chlorobenzoic Acid.

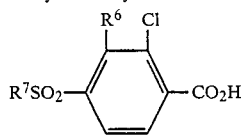

| $R^7$ | $R^6$ | physical Constant (m.p. °C.) |
|---|---|---|
| —$CH_3$ | —$OCH_3$ | 126–129 |
| —$CH_3$ | —$OCH_2CH_3$ | 126–131 |
| —$CH_3$ | —$OCH_2CH_2CH_3$ | 118–123 |
| —$CH_2CH_3$ | —$OCH_3$ | 127–130 |
| —$CH_2CH_3$ | —$OCH_2CH_2CH_3$ | 128–132 |
| —$CH_2CH_2CH_3$ | —$OCH_3$ | 142–145 |
| —$CH_2CH_2CH_3$ | —$OCH_2CH_3$ | 73–78 |
| —$CH_2CH_3$ | —$OCH_2CH_2CH_2CH_3$ | oil |
| —$CH_2CH_3$ | —$OCH_2$—CH—$CH_3$<br>                     $CH_3$ | oil |
| —$CH_2CH_3$ | —OCH—$CH_3$<br>           $CH_3$ | oil |

EXAMPLE 6

3-Alkoxy-4-alkylthio-2-chlorobenzoic Acid

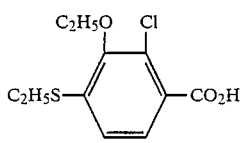

A mixture of the 3-ethoxy-4-ethylsulfonyl-2-chlorobenzoic acid (0.1 mole), potassium carbonate (0.3 mole), diethylsulfate (0.1 mole) and dimethylforamide (150 ml) was stirred at room temperature for 1 hour to give the ethyl ester. Then ethylmercaptan (0.2 mole) was added and the reaction mixture was stirred for 4 days at room temperature to replace the 4-ethylsulfonyl group with a 4-ethylthio group. The reaction mixture was partitioned between methylene chloride and water, and the methylene chloride layer concentrated in vacuo to afford the crude product ester. Hydrolysis of the ester to the acid was accomplished by stirring the ester (0.1 mole) with a base such as sodium hydroxide (0.1 mole) in ethanol (100 ml) at room temperature for 16 hours. The reaction mixture was acidified with 2N hydrochloric acid, and then partitioned between methylene chloride and water. The methylene chloride layer was dried over magnesium sulfate and concentrated in vacuo to afford the acid. m.p. 116°–120° C.

EXAMPLE 7

4-Ethylsulfonyl-3-ethylthio-2-chlorobenzoic acid and 3,4-Bis-ethylthio-2-chlorobenzoic acid

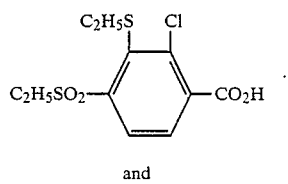

and

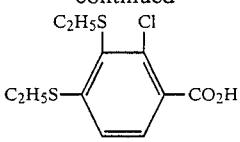

A solution of the 4-ethylsulfonyl-2,3-dichlorobenzoic acid prepared in Example 3 (0.2 mole), ethyl mercaptan (0.8 mole), sodium hydroxide (1 mole) in water (300 ml) was heated at reflux for 24 hours. After cooling, the reaction mixture was acidified with concentrated hydrochloric acid and extracted with methylene chloride. The layers were separated, and the methylene chloride layer was dried over magnesium sulfate. Evaporation of the methylene chloride in vacuo then afforded a mixture of the acids which were esterified to the methyl esters with methanol and sulfuric acid in ethylene dichloride by the procedure of Clinton and Lawkowski, *J. Amer. Chem. Soc.*, 70, 3135 (1948). The esters were then separated via standard chromatographic techniques. Basic hydrolysis of each methyl ester then afforded the 3,4-bis-ethylthio-2-chlorobenzoic acid, m.p. 73°–75° C. and 2-chloro-4-ethylsulfonyl-3-ethylthiobenzoic acid oil.

Additional compounds were prepared by the same procedure as described in Example 7 and are listed in Tables 6 and 7.

TABLE 6
4-Alkylsulfonyl-3-alkythio-2-chlorobenzoic Acid

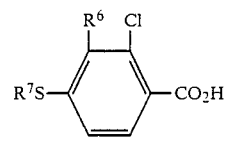

| $R^7$ | $R^6$ | Physical Constant (m.p. °C.) |
|---|---|---|
| $CH_3$ | —$SCH_2CH_3$ | 110–112 |
| $CH_2CH_3$ | —$SCH_3$ | oil |
| $CH_2CH_2CH_3$ | —$SCH_2CH_3$ | oil |

TABLE 7
3,4-Bis-alkylthio-2-chlorobenzoic Acid

| $R^7$ | $R^6$ | Physical Constant (m.p. °C.) |
|---|---|---|
| —$CH_2CH_2CH_3$ | $SCH_2CH_2CH_3$ | semisolid |

The intermediate benzoic acids of this invention can easily be converted to their respective acid chlorides and then to their acid cyanides by the following two reactions. First, a mole of oxalyl chloride in a suitable solvent such as methylene chloride at a temperature of 20° to 40° C. for 1 to 4 hours is heated with a mole of the intermediate acid according to the following reaction scheme:

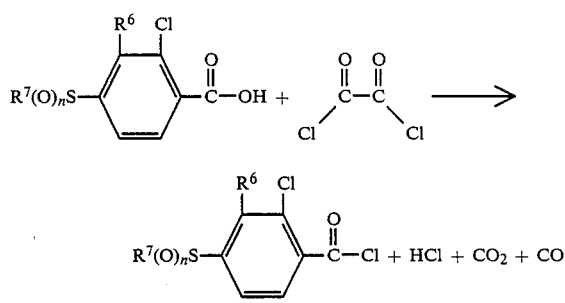

wherein n, $R^6$ and $R^7$ are as defined.

The corresponding benzoic acid cyanide can be easily be prepared from the benzoic acid chloride by reaction with cupous cyanide at a temperature of 150° to 220° C. for 1 to 2 hours according to the following reaction:

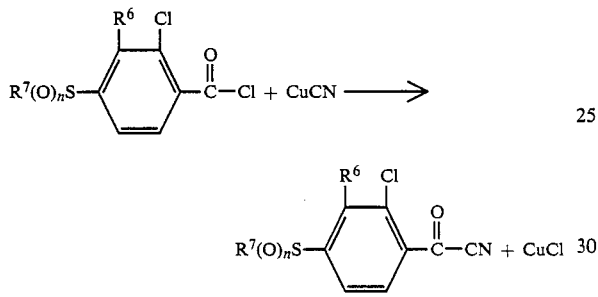

The above-described acid chlorides can be reacted with a 1,3-cyclohexanedione to prepare the above-described herbicidal 2,3,4-trisubstituted benzoyl-1,3-cyclohexane diones according to the following twostep reaction:

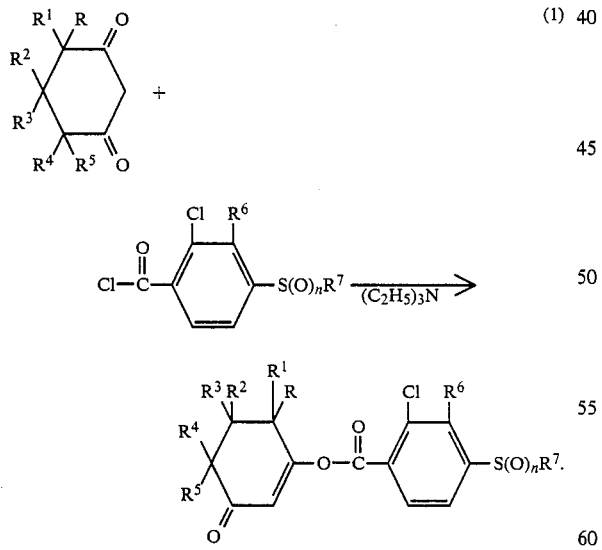

Generally, in step (1) mole amounts of the dione and substituted benzoyl chloride are used, along with a slight mole excess of triethylamine. The two reactants are combined in a solvent such as methylene chloride. The triethylamine is slowly added to the reaction mixture with cooling. The mixture is stirred at room temperature for several hours.

The reaction product is worked up by conventional techniques.

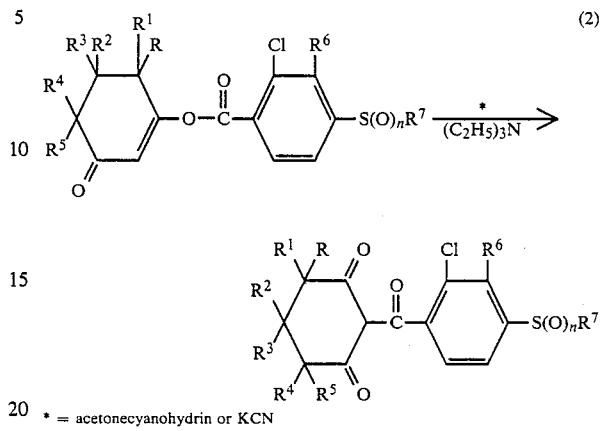

* = acetonecyanohydrin or KCN

Generally, in step (2) a mole of the enol ester intermediate is reacted with 1 to 4 moles of the triethylamine, preferably 2 moles of the triethylamine and up to 0.5 mole, preferably 0.1 mole of a cyanide source (e.g., potassium cyanide or acetonecyanohydrin). The mixture is stirred in a reaction pot for about one hour at room temperature and the desired product is recovered by conventional techniques.

What is claimed is:

1. Compounds having the strucutral formula

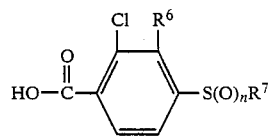

wherein $R^6$ is $C_2$–$C_4$ alkoxy or $C_1$–$C_2$ alkylthio; n is 0 or 2; and $R^7$ is $C_1$–$C_3$ alkyl.

2. Compounds having the structural formula

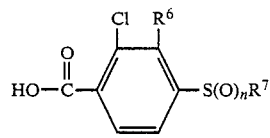

wherein $R^6$ is $C_2$–$C_4$ alkoxy, n is the integer 0 or 2; and $R^7$ is $C_1$–$C_4$ alkyl.

3. Compounds having the structural formula

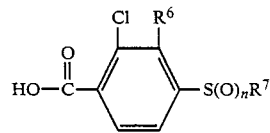

wherein $R^6$ is $C_1$–$C_4$ alkylthio; n is the integer 0 or 2; and $R^7$ is $C_1$–$C_4$ alkyl.

4. A compound having the structural formula

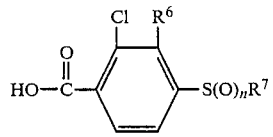

wherein $R^6$ is ethoxy; $R^7$ is ethyl and n is 2.

5. The compounds of claim 2 wherein $R^6$ is ethoxy or n-propoxy; $R^7$ is methyl; and n is 2.

6. The compounds of claim 2 wherein $R^6$ is ethoxy or n-propoxy; $R^7$ is ethyl; and n is 2.

7. Compounds having the structural formula

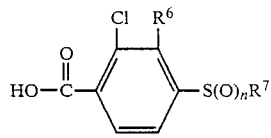

wherein $R^6$ is methylthio or ethylthio; $R^7$ is ethyl; and n is 2.

8. Compounds having the structural formula

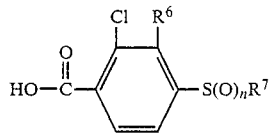

wherein $R^6$ is methylthio; $R^7$ is ethyl or methyl; and n is 2.

* * * * *